United States Patent [19]

Sharvit et al.

[11] Patent Number: 5,093,526
[45] Date of Patent: Mar. 3, 1992

[54] ENVIRONMENTALLY SAFE METHOD OF PREPARING A CERTAIN DIALKYLAMINE

[75] Inventors: Joseph Sharvit, Lehavim; Abraham A. Pereferkovich, Kfar Sava, both of Israel

[73] Assignee: Makhteshim Chemical Works Ltd., Beer Sheva, Israel

[21] Appl. No.: 537,972

[22] Filed: Jun. 14, 1990

[30] Foreign Application Priority Data

Jun. 21, 1989 [IL] Israel .................................. 90704

[51] Int. Cl.$^5$ .................. C07C 213/02; C07C 217/30
[52] U.S. Cl. .................................... 564/399; 564/354; 564/353; 568/630; 568/655; 568/656
[58] Field of Search .................... 564/354, 399, 353; 514/691; 568/629, 630, 655, 656, 776, 774

[56] References Cited

FOREIGN PATENT DOCUMENTS 243038 10/1987 European Pat. Off. .
0296673 12/1988 European Pat. Off. .
1469772 4/1977 United Kingdom .

Primary Examiner—Glennon H. Hollrah
Assistant Examiner—Shailendra Kumar
Attorney, Agent, or Firm—Browdy and Neimark

[57] ABSTRACT

N-n-propyl-N-2-(2,4,6-trichlorophenoxy) ethyl amine is prepared by reacting 2-phenoxy ethanol with thionyl chloride in the presence of a catalytic amount of tetraalkyl ammonium halide optionally in the presence of a solvent to form 2-phenoxy ethyl chloride; reacting the 2-phenoxy ethyl chloride with n-propylamine at a temperature of from 50° C. to 150° C. optionally in the presence of a solvent to form N-n-propyl-N-2-phenoxyethyl amine; selectively chlorinating N-n-propyl-N-2-phenoxyethyl amine with chlorine in the presence of a solvent; and recovering the N-n-propyl-N-2-(2,4,6-trichlorophenoxy) ethyl amine formed.

27 Claims, No Drawings

ENVIRONMENTALLY SAFE METHOD OF PREPARING A CERTAIN DIALKYLAMINE

BACKGROUND OF THE INVENTION

The present invention concerns the improved, environmentally safe process for preparing N-n-propyl-N-2-(2,4,6-trichlorophenoxy)-ethyl amine and its use as an intermediate in the preparation of the fungicide Prochloraz.

According to GB 1,469,772, the classical method of preparing Prochloraz begins with 2,4,6-trichlorophenol. This process suffers from several disadvantages. First of all, the trichlorophenol must be in a highly pure form to avoid the formation of tarry by-products in the subsequent steps of preparing Prochloraz. Second, the processes used to purify 2,4,6-trichlorophenol most often lead to the formation of undesirable chlorinated by-products. Furthermore, the use of 2,4,6-trichlorophenol to prepare Prochloraz requires the reaction of the former under basic conditions, which can also lead to the formation of similar chlorinated by-products.

Recent reports have tried to avoid the problems. Thus, EP 243,038 describes a process of preparing 2,4,6-trichlorophenol involving the slow controlled chlorination of phenol in the presence of a catalyst which is alleged to diminish the formation of the chlorinated by-products.

EP 299,892 describes the chlorination of a chlorophenol using a different type of catalyst.

Nevertheless, even if the formation of unwanted chlorinated by-products are avoided, the standard process for preparing Prochloraz according to GB 1,469,772 involves the need to handle 2,4,6-trichlorophenol and ethylene dibromide—themselves both highly toxic and carcinogenic materials.

OBJECTIVES OF THE INVENTION

It is the objective of the present invention to provide a new, improved and environmentally safe method for the preparation of N-n-propyl-N-2-(2,4,6-trichlorophenoxy)ethyl amine. It is a further objective of the present invention to provide a method for the preparation of this compound without having to handle the highly toxic and carcinogenic 2,4,6-trichlorophenol and ethylene dibromide. A further objective is the provision of a method for the preparation of this compound in high yields substantially free of the chlorinated by-products.

SUMMARY OF THE INVENTION

It has unexpectedly been discovered, that N-n-propyl-N-2-(2,4,6-trichlorophenoxy)-ethyl amine may be prepared comprising the steps of:

1. Reacting 2-phenoxy-ethanol with thionyl chloride in the presence of a catalytic amount of a tetra-alkyl ammonium halide at a temp. of from about 0° C. to 80° C., optionally in the presence of a solvent to form 2-phenoxy-ethyl chloride;
2. Reacting the 2-phenoxy-ethyl chloride with n-propylamine at a temperature of from 50° to 150° C., optionally in the presence of a solvent, to form N-n-propyl-N-2-phenoxyethyl amine;
3. Selectively chlorinating N-n-propyl-N-2-phenoxyethyl amine by reacting it with chlorine in the presence of a catalytic amount of urea at a temperature of from 0° C. to 80° C. in the presence of a solvent to form N-n-propyl-N-2-(2,4,6-trichlorophenoxy)-ethyl amine.
4. Recovering the N-n-propyl-N-2-(2,4,6-trichlorophenoxy)-ethyl amine formed.

DETAILED DESCRIPTION OF THE INVENTION

The reaction process is generally illustrated below on a batch-wise basis:

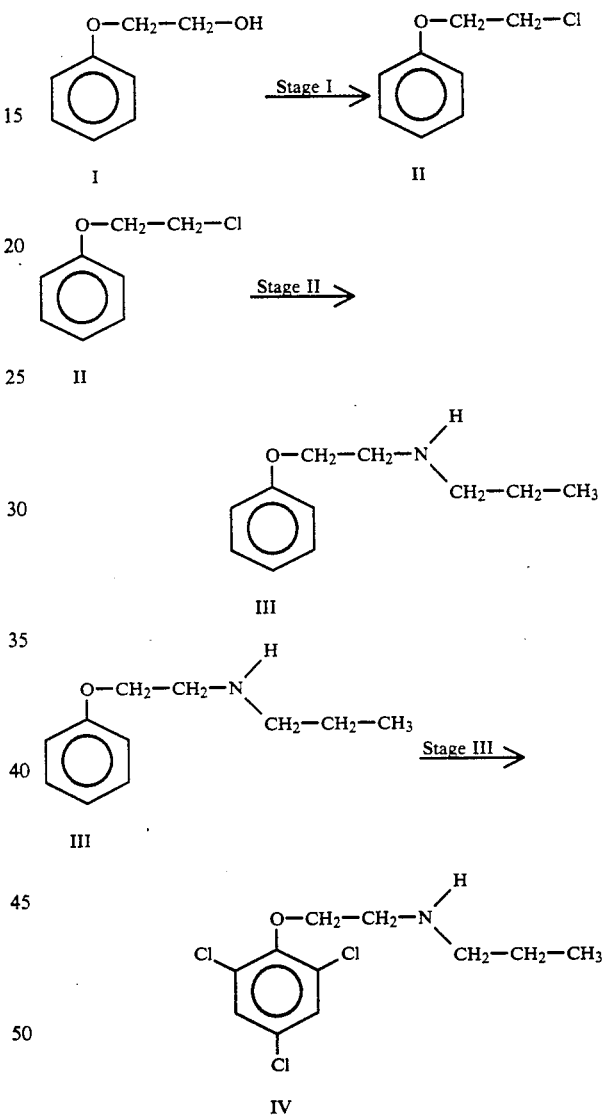

The temperature of reaction of Stage I may range from 0° C. to 80° C., but is preferably in the range of from 10° C. to 50° C.

In carrying out the process of Stage I of the present invention, equimolar amounts of thionyl chloride may be used. However, an excess of up to 20% is preferred to ensure complete reaction. This reaction may be carried out with or without a solvent. If a solvent is used, halogenated hydrocarbons such as chloroform, dichloromethane and carbon tetrachloride are preferred, with dichloromethane being most preferred.

The use of a catalyst such as tetra-alkyl ammonium halide, was found necessary for this stage. The alkyl group of the tetra-alkyl ammonium halide may be chosen from the group consisting of straight or branched alkyl groups having from 1 to 16 carbon atoms, such as methyl, ethyl, propyl, butyl, pentyl, heptyl, decyl and the like, cyclic alkyl groups such as cyclopentyl, cyclo-hexyl, cycloheptyl, cyclodecyl and the like and benzyl. Preferred alkyl groups are straight chain alkyl groups having from 1 to 8 carbon atoms and benzyl. Most pre-ferred are methyl and benzyl, with the preferred halide as chloride. An equally preferred catalyst is benzyl trimethyl ammonium chloride. The tetraalkyl ammonium halide is used in a concentration of 0.5% to 10%, preferably 3%, based on the 2-phenoxyethanol.

The temperature of reaction of Stage II may range from 50° C. to 150° C., but is preferably in the range of from 100° C. to 110° C.

The process of Stage II may be carried out with equimolar amounts of reactants. However, an excess of n-propyl amine is usually used to ensure completion of the reaction. While an excess of 100% to 300% can be used, it is more economical to run the reaction with the excess of about 20% amine.

The process of Stage II may be run without the use of a solvent. However, then a very large excess of amine is required, which increases the work and makes the reaction uneconomical. It is, therefore, preferred to run Stage II in a solvent. Solvents such as ethanol, dimethyl formamide, acetonitrile and a mixture of ethanol-water were found suitable. Preferred solvents are ethanol or ethanol-water, with an ethanol-water mixture most preferred. The ratio of ethanol to water may be 1:1.6 to 1.6:1 and most preferred 1.3 to 1 by volume.

The temperature of reaction of Stage III may range from 0° C. to 80° C., but is preferably in the range of from 25° C. to 40° C. However, the specific preferred temperature depends also on the type of solvent used. This stage may be run in the presence of a suitable solvent, such as chloroform, dichloromethane, carbon tetrachloride, carbon tetrachloride-water and acetic acid. Preferred solvents are carbon tetrachloride-water and acetic acid, with acetic acid the most preferred solvent.

A small amount of urea was found to markedly improve the yield of the reaction and the purity of the product of Stage III. The ratio of urea to N-n-propyl-N-2-phen-oxy-ethyl amine ranges from 1:5 to 1:50, preferably 1:7 to 1:20, by weight.

The final amine product can be isolated as a mineral acid salt, preferably as the hydrochloride acid addition salt, which forms nice white crystals which are easily handled. However, if necessary, the free amine may be isolated by treating the hydrochloride salt with a base such as, for example, aqueous sodium carbonate to neutralize to pH 7, separate the phases and distill the organic layer to yield an oil boiling at 112° C.–114° C. at 0.2 mm Hg.

Thus the present invention affords a process for preparing N-n-propyl-N-2-(2,4,6-trichlorophenoxy)-ethyl amine in high yield, without having to handle the highly toxic 2,4,6-trichlorophenol and ethylene dibromide. The process of the instant invention is of note in that it affords high yields of the N-n-propyl-N-2-(2,4,6-trichlorophenoxy)-ethyl amine whereby the trichlorophenoxy group is formed at as late a stage as possible to avoid any possible decomposition of the trichlorophenoxy moiety of this group to form undesireable chlorinated by-products during reaction. In addition, the amine product may be reacted with phosgene and subsequently with imidazole according to GB 1,469,772 to afford Prochloraz, having essentially no detectable amount undesireable chlorinated by-products.

EXAMPLE 1

Preparation of 2-phenoxyethyl chloride

Into a three-necked flask fitted with a stirrer, dropping funnel, thermometer and reflux condenser, was added 34.7 g 2-phenoxy-ethanol, 75 g dichloromethane and 1.25 g benzyl-trimethyl-ammonium chloride. The mixture was cooled to about 0° C. and 34 g thionyl chloride was added dropwise over a period of 45 minutes. After this addition, the mixture was warmed to room temperature, stirred for an hour and then heated to reflux (50° C.) for an additional three hours. At the end of the reaction (determined by GLC) the mixture was washed with water, an aqueous 10% sodium hydroxide solution and then again with water. The solvent was distilled off to afford 40 g of 2-phenoxy-ethyl chloride in a concentration of 95%.

EXAMPLE 2

The same exact process of Example 1 was repeated without the use of solvent, where the only other difference was, that it was not necessary to remove any solvent after the washings. This afforded a similar yield of 2-phenoxy-ethyl chloride having the same purity.

EXAMPLE 3

Preparation of N-n-propyl-N-2-phenoxyethyl amine

Into a 1-liter glass reactor, which can withstand a pressure of 6 atmospheres, fitted with a stirrer, heat-ing mantle and a pressure gauge, were added 100 g 2-phenoxy ethyl chloride, 150 g propyl amine, 130 ml ethanol and 100 ml water. The reaction was heated to 100° C. for 5 hours, during which time the pressure increased to 2.2 atmospheres. Afterwards the mixture was cooled to 50° C. to lower the pressure, the propyl amine was distilled off, about 200 ml of 20% aqueous HCl was added and the white hydrochloride precipitated out. This afforded 133 g having a purity of 95% in a yield of 93%.

EXAMPLE 4

Preparation of N-n-propyl-N-2-(2,4,6-trichlorophenoxy) ethyl amine

Into a three-necked 500 ml flask fitted with a stirrer, thermometer and a gas bubbler, were added 30 g N-n-propyl N-2-phenoxy-ethyl amine, 200 ml carbon tetrachloride, 1.5 g urea and 30 ml water. Chlorine gas was added with stirring at an initial temperature of 25° C. for 16 hours. At the end of the reaction 200 ml 20% aqueous HCl was added and the precipitated hydrochloride was filtered. The product was slurried with 100 ml carbon tetrachloride and again filtered to afford 41.5 g of N-n-propyl-N-2-(2,4,6-trichlorophenoxy)-ethyl amine hydrochloride having a purity of 95%.

EXAMPLE 5

The process of Example 4 was followed, but only 20 g of N-n-propyl-2-phenoxy-ethyl amine was reacted in 150 ml of acetic acid as solvent, using 3 g urea. Chlorination for 3.5 hours at a temperature of 35° C. to 40° C. afford a product in 85% yield having a purity of 92%.

EXAMPLE 6

The process of Example 5 was followed, but the chlorine gas was added over 2.5 hours at a temperature of 55° C. to afford a product in 81% yield, having a purity of 93%.

While the invention is described in connection with certain preferred embodiments in the above examples, it is understood that it is not intended to limit the invention to these particular embodiments. On the contrary, it is intended to cover all alternatives, modifications and equivalents as may be included within the scope of the invention as defined by the appended claims. Thus, the above examples which include preferred embodiments, will serve to illustrate the practice of this invention, it being understood that the particulars shown are by way of example and for purposes of illustrative discussion of preferred embodiments of the present invention only and are presented in the cause of providing what is believed to be the most useful and readily understood description of procedures as well as of the principles and conceptual aspects of the invention.

We claim:

1. A process for preparing N-n-propyl-N-2-(2,4,6-trichlorophenoxy)-ethyl amine of the formula:

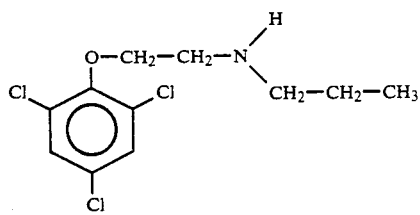

comprising a. reacting 2-phenoxy ethanol of the formula

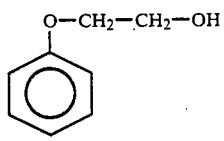

with thionyl chloride in the presence of a catalytic amount of a tetra-alkyl ammonium halide having from 1-16 carbon atoms or benzyl trimethyl ammonium halide at a temperature of from about 0° C. to 80° C. optionally in the presence of a solvent, to form 2-phenoxy-ethyl chloride of the formula:

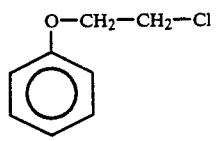

b. reacting the 2-phenoxy-ethyl chloride with n-propyl amine at a temperature of from 50° C. to 150° C. optionally in the presence of a solvent, to form N-n-propyl-N-2-phenoxyethyl amine of the formula:

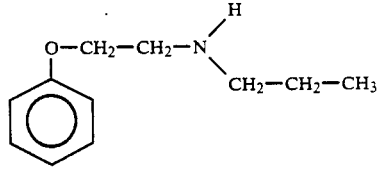

c. selectively chlorinating the N-n-propyl-N-2-phenoxyethyl amine by reacting with chlorine in the presence of a catalytic amount of urea at a temperature of from 0° C. to 80° C. to form N-n-propyl-N-2-(2,4,6-trichlorophenoxy) ethyl-amine; and d. recovering the N-n-propyl-N-2-(2,4,6-trichlorophenoxy)-ethyl amine formed.

2. A process in accordance with claim 1 wherein the solvent of Stage I is a chlorinated hydrocarbon.

3. A process in accordance with claim 1 wherein the solvent of Stage I is chosen from the group consisting of chloroform, dichloromethane and carbon tetrachloride.

4. A process in accordance with claim 1 wherein the solvent of Stage I is dichloromethane.

5. A process in accordance with claim 1 wherein the tetra-alkyl ammonium halide in Stage I is tetra-alkyl ammonium chloride.

6. A process in accordance with claim 1 wherein the alkyl groups of the tetra-alkyl ammonium halide in Stage I are chosen from the group consisting of straight chain alkyl groups having from 1 to 6 carbon atoms.

7. A process in accordance with claim 1 wherein the ammonium halide in Stage I is benzyl-trimethyl-ammonium chloride.

8. A process in accordance with claim 1 wherein the tetra-alkyl ammonium halide in Stage I is present at a concentration of from 0.5% to 10%, based on the 2-phenoxy-ethanol.

9. A process in accordance with claim 1 wherein the temperature of Stage I ranges from about 10° C. to 50° C.

10. A process in accordance with claim 1 wherein the temperature of Stage II ranges from about 100° C. to 110° C.

11. A process in accordance with claim 1 wherein the reaction of Stage II is run in a solvent.

12. A process in accordance with claim 1 wherein the solvent of Stage II is chosen from the group consisting of ethanol, dimethyl formamide, acetonitrile and ethanol-water.

13. A process in accordance with claim 1 wherein the solvent of Stage II is ethanol or ethanol-water.

14. A process in accordance with claim 1 wherein the solvent of Stage II is an ethanol-water mixture.

15. A process in accordance with claim 1 wherein the ratio of ethanol to water in Stage II is 1:1.6 to 1.6 to 1, by volume.

16. A process in accordance with claim 1 wherein the ratio of ethanol to water in Stage II is 1.3:1 by volume.

17. A process in accordance with claim 1 wherein the ratio of 2-phenoxy-ethyl chloride to n-propyl amine of Stage II is 1:1 to 1:3 by weight.

18. A process in accordance with claim 1 wherein the ratio of 2-phenoxy-ethyl chloride to n-propyl amine of Stage II is 1:1.5 by weight.

19. A process in accordance with claim 1 wherein the temperature of Stage III ranges from about 25° C. to 40° C.

20. A process in accordance with claim 1 wherein stage III is run in the presence of a solvent.

21. A process in accordance with claim 1 wherein the solvent of Stage II is chosen from the group consisting of chloroform, dichloromethane, carbon tetrachloride, carbon tetrachloride-water and acetic acid.

22. A process in accordance with claim 1 wherein the solvent of Stage III is carbon tetrachloride-water or acetic acid.

23. A process in accordance with claim 1 wherein the solvent of Stage III is acetic acid.

24. A process in accordance with claim 1 wherein the ratio of urea to N-n-propyl-N-2-phenoxy-ethyl chloride in Stage III is 1:5 to 1:50 by weight.

25. A process in accordance with claim 1 wherein the ratio of urea to N-n-propyl-N-2-phenoxy-ethyl chloride in Stage III is 1:7 to 1:20 by weight.

26. A process for preparing N-n-propyl-N-2-(2,4,6-trichlorophenoxy)-ethyl amine characterized in that:
   a. 2-Phenoxy-ethanol is reacted with thionyl chloride in the presence of benzyl-trimethyl-ammonium chloride in a weight ratio of alcohol to tetra-alkyl-ammonium chloride of 28:1 respectively, in dichloromethane as solvent, at a temp. of from about 10° C. to 50° C. to form 2-phenoxy-ethyl chloride;
   b. the 2-phenoxyethyl chloride is reacted with n-propyl amine in the presence of an ethanol-water solvent at a temperature of from 100° C. to 110° C. to form N-n-propyl-N-2-phenoxy-ethyl amine;
   c. selectively chlorinating the N-n-propyl-N-2-phenoxy-ethyl amine by reaction with chlorine in the presence of urea in a ratio of urea to amine of from 1:7 to 1:20 in a solvent such as acetic acid or carbon tetrachloride-water; and
   d. recovering the N-n-propyl-N-2-(2,4,6-trichlorophenoxy)-ethyl amine formed.

27. A process for preparing N-n-propyl-N-2-phenoxyethyl amine characterized in that:
   a. 2-phenoxy-ethanol is reacted with thionyl chloride in the presence of benzyl-trimethyl ammonium chloride in a weight ratio of alcohol to tetra-alkyl-ammonium chloride of 28:1 respectively, in dichloromethane as a solvent, at a temp. of from 10° C. to 50° C. to form 2-phenoxy ethyl chloride;
   b. the 2-phenoxyethyl chloride is reacted with n-propyl-amine in the presence of an ethanol-water mixed solvent at a temperature of from 100° C. to 110° C., to form N-n-propyl-N-2-phenoxyethyl amine;
   c. recovering the N-n-propyl-N-2-phenoxy-ethyl amine formed.

* * * * *